US009469426B2

(12) United States Patent
Niazi

(10) Patent No.: US 9,469,426 B2
(45) Date of Patent: Oct. 18, 2016

(54) SINGLE-USE STATIONARY BIOREACTORS AND MIXING VESSELS

(75) Inventor: Sarfaraz K. Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 982 days.

(21) Appl. No.: 12/719,836

(22) Filed: Mar. 8, 2010

(65) Prior Publication Data

US 2011/0217767 A1    Sep. 8, 2011

(51) Int. Cl.
| | | |
|---|---|---|
| *C12M 1/36* | (2006.01) | |
| *B65B 63/08* | (2006.01) | |
| *B01F 15/00* | (2006.01) | |
| *C07K 14/00* | (2006.01) | |
| *C12N 1/00* | (2006.01) | |
| *C12N 1/16* | (2006.01) | |
| *C12N 1/20* | (2006.01) | |
| *C12N 5/04* | (2006.01) | |

(52) U.S. Cl.
CPC ........... *B65B 63/08* (2013.01); *B01F 15/0085* (2013.01); *C07K 14/00* (2013.01); *C12M 1/36* (2013.01); *C12N 1/00* (2013.01); *C12N 1/16* (2013.01); *C12N 1/20* (2013.01); *C12N 5/04* (2013.01)

(58) Field of Classification Search
CPC .............................. B01F 11/0065; C12M 1/36
USPC .................................................. 366/239, 275
See application file for complete search history.

(56) References Cited

U.S. PATENT DOCUMENTS

| | | | | |
|---|---|---|---|---|
| 2,406,403 A | * | 8/1946 | Rogers | 526/62 |
| 3,819,158 A | * | 6/1974 | Sharpe et al. | 366/349 |
| 4,550,653 A | * | 11/1985 | Hedenberg | 99/348 |
| 6,190,913 B1 | | 2/2001 | Singh | |
| 6,312,151 B1 | * | 11/2001 | Pendleton | 366/332 |
| 6,544,788 B2 | | 4/2003 | Singh | |
| 7,377,686 B2 | * | 5/2008 | Hubbard | 366/208 |

FOREIGN PATENT DOCUMENTS

WO    00/66706 A1    11/2000

OTHER PUBLICATIONS

Pierce, Bioprocessing J. 3: 51-56 (2004).
Ling et al., "Improvement of Monoclonal Antibody Production in Hybridoma Cells;" Biotechnol. Prog., 19: 158-162 (2003).
Weber et al., "Optimisation of protein expression and establishment of the Wave Bioreactor for Baculovirus/insect cell culture;" Cytotechnology; 38: 77-85 (2002).
Singh, "Disposable bioreactor for cell culture using wave-induced agitation;" Cytotechology; 30: 149-158 (1999).

* cited by examiner

*Primary Examiner* — Jonathan Hurst
(74) *Attorney, Agent, or Firm* — Therapeutic Proteins International, LLC; Sarfaraz K. Niazi

(57) ABSTRACT

Stationary bioreactors and mixing vessels fitted with single-use flexible bags utilizing wave hydrodynamic principle are described for use in every type of biological process and products.

13 Claims, 2 Drawing Sheets

SINGLE-USE STATIONARY BIOREACTORS AND MIXING VESSELS

BACKGROUND

The use of single-use plastic bags in the biological manufacturing, blood-banking and other tissue and cell culture processing is fast becoming the most desirable method as their use obviates the need to clean the vessels and validate them for future operations; with increased demand by the regulatory authorities to provide cleaning validation proof, particularly those of freedom from viruses, it is anticipated that soon, because of higher cost of validation, most of the biological reaction and storage processes will be carried out in single-use flexible plastic bags.

A large number of commercial suppliers are currently marketing these single-use flexible plastic bag systems for biological manufacturing as well as storage of biological fluids such as blood bags; of prime interest to this invention are the mixing systems offered by GE Healthcare as the Wave Bag system wherein a two-dimensional bag is affixed to a rocking platform to mix the contents to produce biological compositions such as culture media and when fitted with appropriate systems, to induce bioreaction in the presence of necessary nutrients and biocatalysts. The U.S. Pat. No. 6,190,913 to Vijay Singh describes the details of the Wave system currently marketed by GE Healthcare. The GE Healthcare Wave Cellbag is intended to be used with a gentle motion and as a result it has been recommended by the manufacturer not to use the system for reactions requiring more vigorous mixing such as required in the fermentation using bacteria or other organisms or cells severely limiting the use of the Wave Cellbag and other similar apparatus in the commercial manufacture of biological products.

Another competing technology utilizes flexible bags attached with stirrers and other implements similar to what is used in the traditional stainless steel fermentors or mixers. In some instances, mixing is achieved by a variety of aeration mechanisms along with mechanical mixing but until now no invention has described a stationary system that will induce mixing inside flexible bags such that the size of the bag can be infinitely variable and the nature and intensity of mixing adjustable to the need of the bioreaction.

SUMMARY OF INVENTION

There are two types of single-use bioreactors available today; one that do not have retaining walls such as the GE Wave system and those that have retaining walls such as the Xcellerex, Sartorius, Millipore and others. The GE bioreactor can only manage media volume of up to 500 L in a 1000 L bag before the physical limit of bag strength or manageability is reached; for the hard-walled support systems, the limitation of providing mechanical stirring devices at larger scale makes them impractical; the largest size of single-use bioreactors available today is offered by Xcellerex at 2000 L at a cost of over two million dollars and with recurring costs comparable to those incurred when using the traditional stainless steel bioreactors.

Despite the obvious savings in capital expenditures and labor costs and improved facility operations, it is unlikely that single-use, single-use technologies will entirely supplant or eliminate the use of stainless-steel systems in bio-manufacturing mainly because of size limitations and physical constraints, in the opinion of the industry leaders. There is therefore an unmet need to invent an apparatus that would allow unlimited substitution of the stainless steel systems by single-use flexible bag systems.

A variety of vessels and methods have been developed over the years to carry out the fermentation of microorganisms, particularly bacteria and yeast, on a commercial scale. Stainless steel fermentation vessels of hundreds of thousands of liters are not uncommon, with the fermentation methods including batch, fed-batch, and continuous or semi-continuous perfusion. The cells within these vessels are desirably kept in suspension, typically by rotating stirring blades located within the vessel, with gas exchange facilitated by the injection of air, oxygen or carbon dioxide into the vessel. There are several drawbacks to this design. One is the introduction of shearing forces through the stirring blades and the cavitations of miniscule air bubbles, both being detrimental to more sensitive cell types or organisms. Also, these vessels should be rigorously cleaned between production runs to prevent cross-contamination, the latter being time consuming and requiring validation for individual cultures. Furthermore, the cost of stirred fermentors is relatively high on a volume basis, and thus these fermentors are commonly used over long periods of time. This, however, increases the risk of undesirable infection of mechanical failures. Perhaps most significantly, the optimization of culture conditions for stirred fermentors in a small scale cannot be transferred in a linear way to commercial scale production. For example, the fluid dynamics, aeration, foaming and cell growth properties change when the scale increases. In addition, for more delicate cell types or organisms, a large-scale stirred fermentation vessel is not a viable device, even when more subtle stirring techniques such as airlift fermentors are used.

These drawbacks have led to the development of single-use fermentors. Examples of such single-use fermentors are systems based on wave agitation. See, e.g., U.S. Pat. No. 6,544,788; PCT Publication WO 00/66706. This type of fermentor may be used to culture relatively sensitive cells such as CHO cells (e.g., Pierce, Bioprocessing J. 3: 51-56 (2004)), hybridoma cells (e.g., Ling et al., Biotech. Prog., 19: 158-162 (2003)), insect cells (e.g., Weber et al., Cytotech. 38: 77-85 (2002)) and anchorage-dependent cells (e.g., Singh, Cytotech. 30: 149-158 (1999)) in a single single-use container. Such single-use units are relatively cheap, decrease the risk of infection because of their single use and require no internal stirring parts as the rocking platform upon which these containers reside during use induces wave-like forms in the internal liquid, which facilitates gas exchange. However, this principle cannot be expanded to the size of hundreds of thousands of liters (such as the industrial fermentors) but are currently available from 1 liter to 500 liters (total volume of the single-use bag, available from Wave Biotechnology AG, Switzerland; Wave Biotech Inc., USA). Moreover, the hydrodynamics for each size of single-use bag will differ as a result of differences in depth and height. Therefore, the use of these single-use bags requires optimization and re-validation of each step in an up scaling process.

Thermo Fisher Hyclone was the first to introduce the single-use, single-use bioreactor concept and offers various sizes of vertical, cylindrical bioreactor bags that are designed to fit into a stainless outer vessel support with a heating jacket and a single-use mixing mechanism. Aeration, mixing, and biosensor probes are introduced into the bag through welded elastomer sleeves.

Sartorius Stedim and GE Healthcare/Wave manufacture bioreactor bags in a flat configuration agitated by the motion of a rocker platform. Like the Thermo Fisher Hyclone configuration, mixing, aeration, and probes are inserted into the Wave and Sartorius Stedim through welded bag ports.

ATMI Life Sciences recently introduced a rectangular-shaped single-use bioreactor bag with a top-mounted agitator rod.

Xcellerex manufactures a single-use bioreactor bag that fits into a support shell with a magnetically coupled bottom agitation system (stirred-tank) for mixing.

Although bioreactor systems and related processes are known, improvements to such systems and processes would be useful in the preparation of a variety of products produced from a biological source. A similar situation arises when flexible bags are used for the purpose of mixing the contents such as in the preparation of culture media or buffers; the long-time use of flexible plastic bags is well known in the blood banking industry where often the need arises for the mixing of contents to reduce the degradation of the contents. Yet another significant application that pertains the mixing function arises in the manufacture of recombinant proteins wherein the protein is allowed to unfold in a very dilute solution at low temperature. To obtain the optimal yield upon refolding the solution must be gently shaken during the refolding period. All of these operations are dependent on the efficiency of the mixing methods.

The technology for mixing and aeration also forms the core of the engineering design that allows biological reactions to take place in vessels called fermentors or bioreactors. Hard-walled stainless steel reactors are available in all sizes from a few liters to thousands of liters and are the mainstay of the manufacturing of biotechnology products. However, the flexible plastic bag use (without retaining walls) is severely limited by the size of the batch as it becomes mechanically unmanageable to provide a suitable mixing cycle in the container because of the large size and weight on the platform that imparts the motion to the flexible bag. Any type of mechanical motion whether it is rocking, orbital or reciprocal requires a tremendous amount of energy to move the flexible plastic container filled with media.

The requirement of high agitation of liquid media in the fermentation of microorganisms is one reason why flexible containers should be used for growing microorganisms. The difficulty arises in shaking vigorously the entire container that may weight hundreds of even thousands of pounds producing stress on the walls of the container besides needing very large mechanical systems to operate these shaking protocols. The instant invention resolves this problem by keeping the bag stationary on a flat surface and only creating motion inside the bag by a squeeze motion that produces many different types of mixing, from very gentle to very vigorous, the latter being a requirement of growing microorganisms and thus allowing the use of flexible containers for the purpose of growing microorganisms.

The instant invention capitalizes on a well-known phenomenon of liquid wave propagation wherein a movement created in one part of a continuous liquid media travels and spreads to all other parts of liquid media.

To remove the limitation of the size of the mixing or bioreacting bag in single-use environment, the instant invention eliminates the need for providing any motion at all to the bag. Instead, the mixing motion, whether in the form of a gentle wave or intense turbulence, is induced inside the bag by applying compression at one end of the bag filled with liquids and by applying such action repeatedly in a cyclical manner, a wave motion is created that allows gentle mixing of components in the singe-use containers; however the amplitude and frequency of edge compression can easily lead to extreme turbulent motion inside the bag.

Thus a preferred embodiment of this invention is a method of mixing contents in flexible plastic containers by applying compression force along one edge of the bag and then reversing the compression on the other side to create a wave motion.

In another preferred embodiment of the instant invention the compression at the edge of the bag is provided at all four edges in a cycle that produces vortex inside the bag.

In another preferred embodiment the instant invention provides a method of mixing and bioreacting any size of flexible containers.

In another preferred embodiment the instant invention provides a method for fermentation and bioreaction for growth of cells and microorganisms.

In another preferred embodiment the instant invention provide a method for mixing of fluids in flexible bags such that the contents are kept homogenous.

In another preferred embodiment the instant invention provides a method for refolding of proteins in recombinant manufacturing of drugs wherein refolding media is stored at low temperature and mixed gently for extended time.

In another preferred embodiment the instant invention provides a method of extending the storage life of biological products whereby gentle mixing is required to prevent degradation.

DETAILS OF INVENTION

The instant invention is based on several essential components. First, there is a two or three-dimensional flexible bag that can contain various volumes of liquid products or media. The flexible bag may additionally contain other features as required for the aeration of media, exhaust of gases, introduction of culture media, filtration and removal of media or any other such feature that may be required to achieve the intent of the process. For example, one such instant will the Bio Bag supplied by Wave Systems that is available in sizes ranging from 5 L to 1000 L. This bag can be used without any modification in the instant invention. However, the most expensive part of the Wave System involves a rocking platform that also limits the size of liquid product handled to about 500 L since beyond this size, it becomes mechanically prohibitive and thus restricts the applications of flexible bags in bio-manufacturing. Similarly, flexible bags of any design, shape or form can be used in the instant invention without further modification. However, in all such instances the mixing mechanism is replaced with the method described in the instant invention.

Secondly, a support surface is provided for the flexible bags of a size such that the flexible bags would fit within the dimensions of the support surface.

Third, the support surface is provided with flaps that also act as side support in the form of short walls of a size such that when the flexible bag is fully inflated, the walls will prevent it from tipping or falling outside.

Fourth, the flaps described in the feature Three are attached to the supporting surface by a hinge that will allow movement of the flaps in both directions; the flaps are pulled down when loading the supporting surface and then raised after the loading of the flexible bag.

Fifth, the flaps can be moved horizontally to bring them closer to the flexible containers to provide better contact and efficiency of operation.

Sixth, the flaps area connected to diagonally opposite flaps by a mechanical means such that the movement of one flap also forces the movement of the opposing flap in opposite direction.

Seventh, the moveable flaps are provided with at least one means of movement in the direction of the bag and using a motorized cam or linear actuator that can be adjusted for amplitude and frequency.

Eight, the instant invention is operated by pushing the flaps either in one dimension of in both dimensions in a reciprocal motion such that the flexible bag is poked by the movement of flaps and this action is followed by a similar application of force on the opposite of the flexible bag; the repeated application of this force thus creates a repeatable motion within the liquid contained in the flexible bag.

Nine, the instant invention optionally provides means of keeping the support surface hot or cold as may be required by the process by introduction of means of heating or cooling attached to the underside of the support surface.

Figure 1:
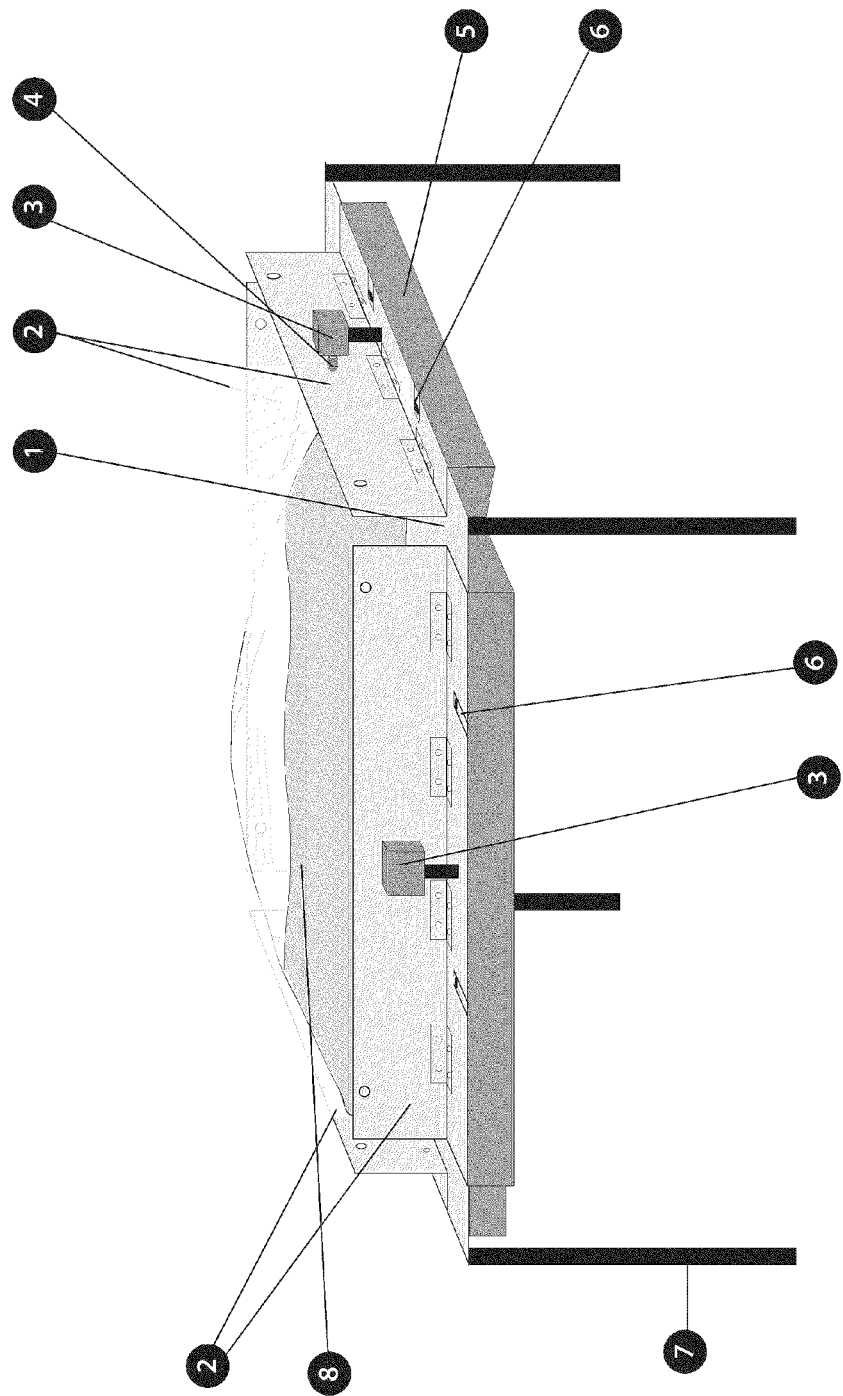
FIG. 1 is the angle view of the bioreactor showing the flaps, the motorized drive to move them to affect hydrodynamic motion inside the flexible bag.

As a preferred embodiment FIG. 1 describes the construction the apparatus. A flat support surface 1 is connected to flaps 2 on all four sides by hinges; the flaps are attached to a linear actuator 3 through its push and pull rod 4 such that upon activating the actuator, the flap 2 is moved vertically in either direction. The flat surface 1 is provided with means of heating or cooling it as feature 5 and adjusting the position of flaps 2 on the adjustment rail 6 since the size of flexible bag may change requiring moving the flaps closer to the bag; the entire apparatus rests on legs 7 and contained inside the apparatus is a flexible bag 8.

Figure 2:
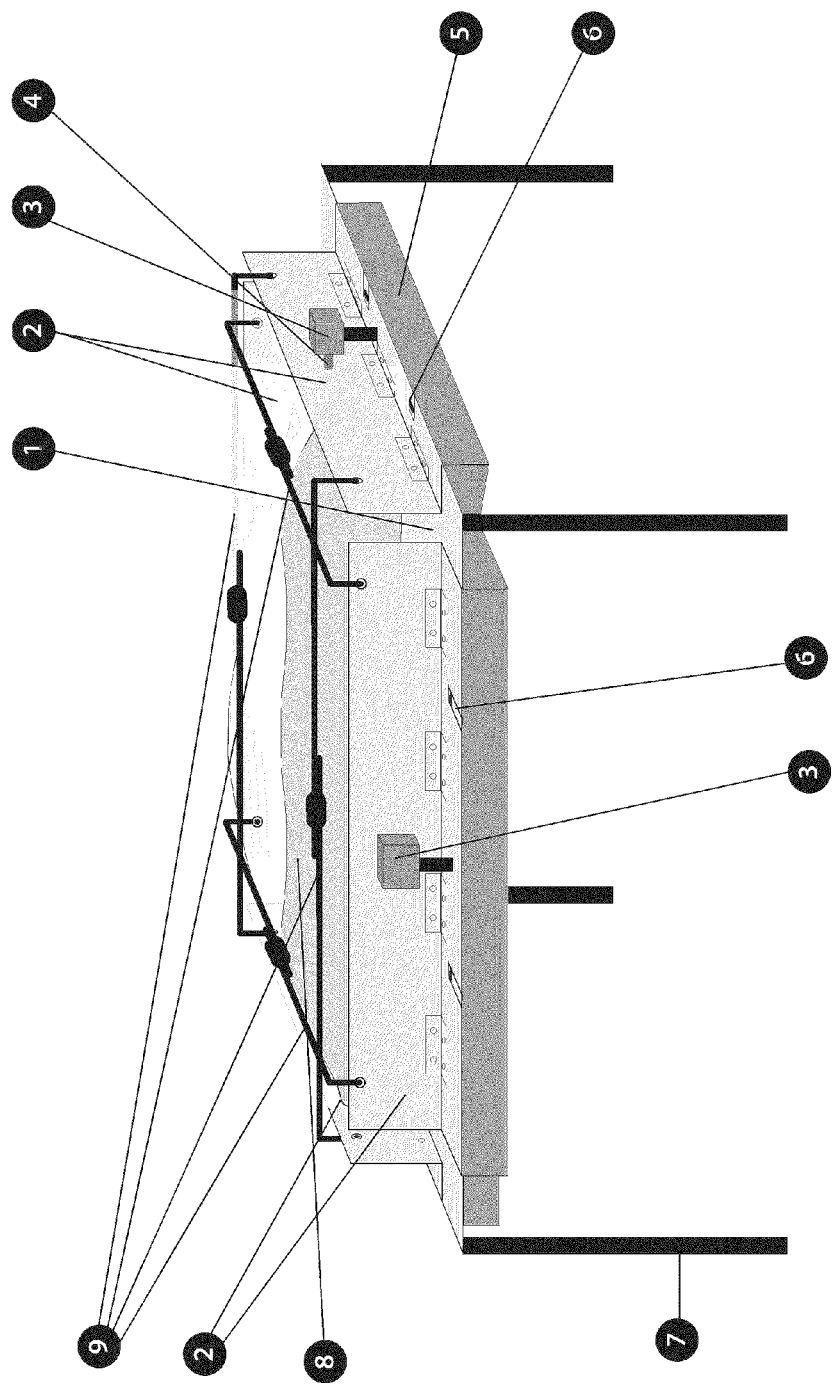
FIG. 2 is the angle view of the bioreactor as described in FIG. 1 and including interconnecting rods to move opposite flaps in synchronization.

FIG. 2 describes the same features as shown in FIG. 1 and additionally includes inter-connecting rods 9, which when installed allow synchronous movement of opposite flaps using only linear actuator 3 for the operation of two opposite flaps.

In a typical operation, first the flaps 2 on one of each of the long and short side of the flat surface 1 are opened down to allow easy access to a flexible container 8 filled with culture media and attached to other systems to aerate the culture will be placed on surface 1 and the surface 1 heated or cooled by operating feature 5, which is likely to be a block through which either cold or hot water is passed or contains a separate resistance type heater for heating surface 1. Now the flaps 2 are brought in close proximity to the flexible bag by adjusting the nuts on railing 6. If synchronized movement is required, the flaps 2 are interconnected with opposite flaps by means of connecting rods 9, which are also adjustable in size. Now once the assembly is complete, the apparatus is operated by switching on the power to the linear actuator 3, which pushes flaps to a fixed downward position and with frequency adjusted by the control of linear actuator 3. Once the reaction process is complete, the linear actuator 3 is stopped, the flaps 2 folded down and the flexible bag 8 either removed from the surface 1 with culture media or the culture media is first removed from the bag by a peristaltic pump through a tube inserted inside the bag (not shown).

In another embodiment, the flexible bag placed on support surface 1 contains a protein solution undergoing refolding, when all operations described above will be applied except that the movement of flaps will be slow and the surface 1 kept cold to a temperature of about 8 C-10 C.

In another embodiment, the flexible bag placed on support surface 1 is used to mix culture media or buffer wherein materials will be introduced in the bag, which is then allowed to mix the ingredients through movement of fluid, with moderately agitation.

In another embodiment, the contents of flexible bag on support surface 1 are kept mixed through the action of flaps 2 for prolonged period of time during storage of biological products.

What is claimed is:

1. A method of inducing a wave-type mixing motion inside a flexible container comprising:

a. supplying a flat, horizontal stationary surface;

b. placing a flexible container comprising a top and bottom surface on the stationary surface, wherein the flexible container is capable of containing a liquid medium;

c. pivotally attaching at least one movable flap to the stationary surface, wherein the movable flap comprises a rigid surface attached to the stationary surface by a hinge that allows the rigid surface to pivot to apply sufficient force to compress the top surface of the flexible container along an edge and then reverse direction of movement of the flap;

d. operating the at least one movable flap periodically such that a wave type mixing motion of the liquid medium occurs within the flexible container; and e. wherein the at least one movable flap includes a first moveable flap and a second moveable flap, the first moveable flap mechanically connected to the second moveable flap such that movement of the first moveable flap causes movement of the second moveable flap.

2. A method of inducing a reciprocal mixing motion inside a flexible container comprising:

a. supplying a flat, horizontal stationary surface;

b. placing a flexible container comprising a top and bottom surface on the stationary surface, wherein the flexible container is capable of containing a liquid medium;

c. pivotally attaching at least two movable flaps at opposite ends of the stationary surface, wherein the movable flaps each comprise a rigid surface attached to the stationary surface by a hinge that allows the rigid surface to pivot to apply sufficient force to compress the top surface of the flexible container along an edge and then reverse direction;

d. operating the at least two movable flaps periodically such that a reciprocal mixing motion of the liquid medium occurs within the flexible container; and e. wherein the at least two movable flaps are mechanically connected such that movement of one of the at least two movable flaps causes movement of the other of the at least two movable flaps.

3. A method of inducing an orbital mixing motion inside a flexible container comprising:

a. supplying a flat, horizontal stationary surface;

b. placing a flexible container comprising a top and bottom surface on the stationary surface, wherein the flexible container is capable of containing a liquid medium;

c. pivotally attaching four movable flaps to the stationary surface, wherein the flaps are attached to the stationary surface by hinges that allow the flaps to pivot to apply sufficient force to compress the top surface of the flexible container sequentially along each edge and then reverse direction;

d. operating the four movable flaps periodically such that an orbital mixing motion of the liquid medium occurs within the flexible container; and e. wherein opposite flaps of the four movable flaps are mechanically connected such that movement of one of the opposite flaps causes movement of the other of the opposite flaps.

4. A method of inducing a vertical mixing motion inside a flexible container comprising:

a. supplying a flat, horizontal stationary surface;

b. placing a flexible container comprising a top and bottom surface on the stationary surface, wherein the flexible container is capable of containing a liquid medium;

c. pivotally attaching two movable flaps at opposite ends of the stationary surface, wherein the flaps are attached to the stationary surface by hinges that allow the flaps to pivot to apply sufficient force to compress the top surface of the flexible container simultaneously along an edge and then reverse direction d. operating the two movable flaps periodically such that a vertical mixing motion of the liquid medium occurs within the flexible container; and e. wherein the two movable flaps are mechanically connected such that movement of one of the two movable flaps causes movement of the other of the two movable flaps.

5. The method of any one of claims 1 to 4, wherein the movable flap(s) are controlled by an automated mechanism.

6. The method of claim 1, wherein the at least one movable flap further acts as a sidewall to prevent the flexible container from tipping or falling off of the stationary surface.

7. The method of claim 2, wherein the at least two movable flaps further act as sidewalls to prevent the flexible container from tipping or falling off of the stationary surface.

8. The method of claim 3, wherein the four movable flaps further act as sidewalls to prevent the flexible container from tipping or falling off of the stationary surface.

9. The method of claim 4, wherein the two movable flaps further act as sidewalls to prevent the flexible container from tipping or falling off of the stationary surface.

10. The method of claim 1, wherein the at least one movable flap is horizontally adjustable along the stationary surface to accommodate flexible bags of different sizes.

11. The method of claim 2, wherein the at least two movable flaps are horizontally adjustable along the stationary surface to accommodate flexible bags of different sizes.

12. The method of claim 3, wherein the four movable flaps are horizontally adjustable along the stationary surface to accommodate flexible bags of different sizes.

13. The method of claim 4, wherein the two movable flaps are horizontally adjustable along the stationary surface to accommodate flexible bags of different sizes.

\* \* \* \* \*